(12) United States Patent
Hartsfield

(10) Patent No.: US 8,047,375 B1
(45) Date of Patent: Nov. 1, 2011

(54) DIAPER CHANGING KIT

(76) Inventor: Christopher S. Hartsfield, Valrico, FL (US)

( * ) Notice: Subject to any disclaimer, the term of this patent is extended or adjusted under 35 U.S.C. 154(b) by 0 days.

(21) Appl. No.: 12/658,432

(22) Filed: Feb. 9, 2010

Related U.S. Application Data

(60) Provisional application No. 61/207,374, filed on Feb. 11, 2009.

(51) Int. Cl.
*B65D 69/00* (2006.01)

(52) U.S. Cl. .................................................. 206/581

(58) Field of Classification Search .............. 206/581, 206/823, 438, 494
See application file for complete search history.

(56) References Cited

U.S. PATENT DOCUMENTS

| | | | |
|---|---|---|---|
| 2,558,955 A * | 7/1951 | Hilton | 206/763 |
| 2,825,208 A * | 3/1958 | Anderson | 190/109 |
| 3,732,955 A | 5/1973 | Carter et al. | |
| 4,702,378 A * | 10/1987 | Finkel et al. | 206/581 |
| D341,027 S | 11/1993 | Godden et al. | |
| 5,443,161 A | 8/1995 | Jonese | |
| 5,638,957 A * | 6/1997 | Brasier | 206/581 |
| 5,725,382 A * | 3/1998 | Walter et al. | 434/258 |
| 6,168,022 B1 | 1/2001 | Ward et al. | |
| 6,213,304 B1 | 4/2001 | Juliussen | |
| 6,298,993 B1 | 10/2001 | Kalozdi | |
| 6,540,084 B2 | 4/2003 | Silvers | |
| 6,723,080 B1 | 4/2004 | Habib et al. | |
| 6,745,895 B2 | 6/2004 | Silvers | |
| 7,194,848 B2 | 3/2007 | Snell | |
| 7,204,368 B2 | 4/2007 | Cheaure et al. | |
| 7,207,439 B2 * | 4/2007 | Casella | 206/459.1 |
| 7,469,521 B2 | 12/2008 | Cheaure et al. | |
| 7,597,198 B1 * | 10/2009 | Foster | 206/575 |
| 2002/0157972 A1 * | 10/2002 | Gallo et al. | 206/232 |
| 2006/0032782 A1 * | 2/2006 | Suh et al. | 206/581 |
| 2006/0283205 A1 | 12/2006 | Carriere | |
| 2007/0233032 A1 | 10/2007 | Rau | |
| 2008/0108965 A1 | 5/2008 | Christensen et al. | |
| 2008/0289993 A1 | 11/2008 | Flannery | |

* cited by examiner

*Primary Examiner* — Jacob K Ackun

(74) *Attorney, Agent, or Firm* — Frijouf, Rust & Pyle, P.A.

(57) ABSTRACT

A diaper changing kit is disclosed for assisting an individual in cleaning a soiled child. The diaper changing kit comprises a container defining an interior chamber and a container aperture for accessing the interior chamber. A tool cleans the soiled child and provides both a functional and a humorous characteristic. A first body item positions on the individual and provides both a functional and a humorous characteristic. A second body item positions on the soiled child and provides both a functional and a humorous characteristic. The tool, the first body item and the second body item are positioned within the container for transporting.

12 Claims, 4 Drawing Sheets

DIAPER CHANGING KIT

CROSS-REFERENCE TO RELATED APPLICATIONS

This application claims benefit of U.S. Patent Provisional application Ser. No. 61/207,374 filed Feb. 11, 2009. All subject matter set forth in provisional application Ser. No. 61/207,374 is hereby incorporated by reference into the present application as if fully set forth herein.

BACKGROUND OF THE INVENTION

1. Field of the Invention

This invention relates to diaper changing and more particularly to a diaper changing kit that is both functional and humorous.

2. Background of the Invention

The task of diaper changing of babies is generally an easily acceptable task for women, yet a formidable task for many men, especially first time fathers. A series of devices have been produced which attempt to make the task more easily accomplished. As with many other unrelated tasks, humor tends to be introduced simply because the circumstances produce an environment which is conducive to humor. The following U.S. Patents and Patent Applications are examples of attempts of the prior art to increase the ease of completing the diaper changing task.

U.S. Pat. No. 3,732,955 to Carter et al discloses an upwardly opening open-top housing including opposite side and end walls interconnected at their lower marginal edge portions by means of a bottom wall extending therebetween with a top wall being provided and removably positionable over the open upper side of the housing for closing the latter. The inside of the housing includes parallel spaced upstanding partitions dividing the housing interior into three longitudinally spaced compartments and one of the end compartments includes a horizontal partition spaced at least slightly above the bottom wall of the housing and having openings formed therethrough whereby upright containers such as feeding bottles and jars of baby food resting on the bottom wall and projecting upwardly through the horizontal partition may be supported against lateral shifting into engagement with each other. Also, the underside of the top wall of the housing includes means by which an inverted facial tissue box may be removably supported from the top wall for ready dispensing of facial tissues therefrom when the top wall is swung to its open position.

U.S. Pat. No. 4,702,378 to Finkel et al. discloses a single use, disposable kit receives, and retains, toiletries and a diaper for the care of a baby in a sanitary, tamper-proof fashion. The kit is executed in a thin plastic film that is folded over upon itself so that the toiletries and diaper are enveloped within the interior of the kit and are protected against degradation.

U.S. Pat. No. 5,443,161 to Jonese discloses a disposable kit having a plurality of baby care supplies stored within a moisture impermeable enclosure. The kit includes supplies for two complete diaper changes, and it is easy to manufacture and extremely compact. A tear line, fabricated from a weakened portion within one of the enclosure walls, permits for easy access to the contents stored within the enclosure. These contents are two diapers, two moisture impermeable disposal bags, two wet wiping elements, baby powder, and baby cream. To provide the enclosure with a uniform and pliable surface, the two diapers are arranged to be substantially entirely in contact with opposing sides of the enclosure.

U.S. Pat. No. 6,168,022 ward et al. discloses a baby supplies carrying case including a panel of fabric having a first fold line extending across the panel and a second fold line in spaced parallel relationship to the first fold line. The first fold line and sides of the panel define a first section in the panel. The first and second fold lines and sides of the panel define a second section of the panel. The second fold line and sides of the panel define a third section. The panel is foldable such that the first section overlies the second section. The panel is foldable such that the second section overlies the first section. The third section includes fasteners for maintaining the third section in overlying relationship to the first section. The panel has a first pocket formed therein and located within the first section. The panel has a second pocket opening in the second section and extending into the third section. A third pocket overlies the first pocket and is located within the first section. The first pocket is suitable for receiving a wipe case therein or other similar sized items. The second pocket is suitable for receiving a diaper therein or other similar sized items. A handle is connected to the panel and extends outwardly therefrom so as to allow the case to be suspended from an exterior object.

U.S. Pat. No. 6,213,304 to Juliussen discloses an infant care tote bag for holding infant care supplies therein. The infant care tote bag includes a pair of body portions pivotally coupled together. An elongate shoulder strap is provided having a pair of opposite V-shaped ends which are detachably attached to the body portions.

U.S. Pat. No. 6,298,993 to Kalozdi discloses a diaper bag providing an enclosure includes a top, bottom, front, back and side panels. The front panel is attached to the side and top panels by a zipper, allowing access to an interior compartment. Two back panel interior compartments are made of mesh and may be sealed by separate zippers. Front panel interior compartments include a full-width zipped pocket upon which are mounted four pleated front panel pockets made of mesh with elastic closures. A changing pad is carried in the bottom of the interior compartment, and may be removed for use. A flip-out compartment array is attached to an upper portion of the front wall. When the enclosure is opened, the flip-out compartment array may be removed from the interior compartment. A support assembly carries the entire diaper bag by a tab located on an upper portion of the flip-out compartment, thereby orienting all compartments for easy access. At least one base interior compartment is attached to the bottom panel. Front and back external compartments are defined between the front and back panels and a clear plastic and a mesh panel, respectively, and are accessible without opening the enclosure. A tethered compartment is attached to the interior of the enclosure by a line, and includes a zippered pocket which is removable from the enclosure for easier access.

U.S. Pat. No. 6,540,084 to Silvers discloses a compact portable pack for holding diapers, wet baby wipes, and reclosable disposable bags. The pack comprises a container base of plastic material comprising a rectangular sidewall and a partition wall. The rectangular sidewall extends between two opposing ends and includes pairs of parallel sides. The partition wall intersects all sides separating the container base into a wipe compartment at one end and a diaper compartment at the other end. The wipe compartment holds wet baby wipes while the diaper compartment holds diapers. Lids of plastic material are integrally hinged to the rectangular base on different sides and at opposite ends of the container base. Each lid is movable between open and closed positions. In the closed position the lids engage the container base to close the diaper compartment and wipe compartment. A resilient clip is supported by the lid covering the diaper compartment and retains reclosable disposable bags.

U.S. Pat. No. 6,723,080 to Habib et al. discloses a prepackaged diaper changing kit which is compact and convenient to carry and use and which is capable of being both dispensed from a conventional vending machine, as well as being displayed on shelves and sold in conventional retail establishments. A preferred embodiment of this prepackaged diaper changing kit includes a disposable diaper, at least one (1), and more preferably two (2), prepackaged moist baby wipes, a prefolded baby liner, a prepackaged instant hand sanitizer and a prefolded disposable plastic bag. These items are preferably prepackaged together in a durable waterproof outer wrapper, such as an opaque plastic outer wrap film. The prepackaged diaper changing kit in accordance with the present invention provides all of the supplies needed to change a diaper for, for example, a newborn or infant, and, when finished, allows the user to secure and discard the dirty or wet diaper, as well as the used moist baby wipes and other left over packaging materials, in a safe and convenient manner.

U.S. Pat. No. 6,745,895 to Silvers discloses an apparatus for assisting in the changing of diapers for a baby in the form of a portable diaper caddy. The tray has a base adapted to rest upon a surface. The tray includes multiple selectively sized compartments including a diaper compartment in the tray adapted to contain a plurality of diapers, a pad compartment in the tray adapted to contain a baby changing pad, and a wipe compartment in the tray adapted to contain a plurality of wet baby wipes. A lid covers the wipe compartment, the lid sealing against a top portion of the wipe compartment to prevent evaporation of liquid contained in the wet baby wipes. A handle extends from the tray to allow persons to grasp the tray for carrying the tray.

U.S. Pat. No. 7,194,848 to Snell discloses a diaper folded about lengthwise foldlines between side elastic banded edges and is folded along a widthwise foldline such that the diaper length is reduced by at least 50%. A central portion of the diaper is visible and the remainder thereof is hidden from view within the folds. Thereafter, a height of the folded diaper is reduced by compressing the diaper with opposed surfaces of a press and the diaper is sealed within an encasement having an interior volume that closely corresponds to the diaper. Sealing is done under a vacuum sufficient to result in further compression of the diaper to a very firm and dense state in which the surface of the diaper is hard. The vacuum-sealed diaper is packaged with a diaper accessory with the diaper and accessory located within separate interior spaces isolated by an air impermeable material such that a pressure differential may exist therebetween.

U.S. Pat. No. 7,204,368 to Cheaure et al, discloses a package for consumable products includes an enclosure having a top, a bottom and opposing side portions, the enclosure containing one or more items chosen from a first set of consumable products, a first seal disposed about, and spaced inwardly from the periphery of, three adjacent side portions of the enclosure, a resealable closure adjacent the fourth side of the enclosure, the enclosure being folded so that the periphery of the fourth side is disposed adjacent to and parallel with the periphery of the side opposite to the fourth side, a second seal formed at the periphery of the folded sheets to form a second compartment of a size sufficient to house one or more items chosen from a second set of consumable products, and a third seal formed inwardly of the second seal and spaced outwardly of the first seal, the third seal being a perforated seal that enables detachment of a strip of material disposed between the periphery of the sheets and the third seal. The second compartment is enclosed within said first compartment, and the first and second sets of consumable goods comprise edible items, diaper changing items, or first aid items.

U.S. Pat. No. 7,469,521 to Cheaure et al. discloses a container and a method of making the container. The process consists of arranging two sheets of material in face-to-face relationship with mating fastening elements carried by the sheets being disposed adjacent one another. Three sides of the sheets are sealed together to form an enclosure, a product is placed in the enclosure, the fastening elements are engaged to seal the fourth side of the sheets, the sealed enclosure is folded over on itself and a second product is placed between the now facing sides of the enclosure, and the folded over enclosure is sealed with a breakable seal disposed outside of the first seal such that the first and second products are captured and sealed within the so-formed container. An embodiment of the container is disclosed which comprises a diaper changing kit enclosing a diaper and at least one of a variety of baby changing accessories.

U.S. Patent Application 2006/0283205 to Carriere discloses a 3-in-1 diaper bag/cooler/bottle warmer or baby food warmer having three separate compartments. Two outside zip closed pockets each have insulated foil lining and sewn in mesh pockets. One compartment on one side of the bag has cooling packs such as ice packs in the compartment to keep milk and baby food cold. Another compartment on another side of the bag also has wrap around heating packs that can warm up a chilled bottle or jar of baby food. The center compartment between the two outside compartments holds a baby's essentials that will be needed while away from home, such as diapers, wipes, clothes, and blankets and serves as in insulating layer between the other two compartments.

U.S. Patent Application 2007/0233032 to Rau discloses a disposable diaper changing kit including a disposable package having a front wall and a rear wall of double wall construction including an inner rear wall and an outer rear wall. The front wall and inner rear wall are joined to one another to define a first pocket, with their top edges being releasably joined to one another by a releasable fastener, such as a bead and groove-type fastener, for example. The inner rear wall and outer rear wall are joined around their peripheral edges to define a second pocket. A disposable diaper and a disposable diaper changing mat are received within the first pocket. At least one disposable baby wipe is packaged within the second pocket. A slot is formed by perforations through the outer rear wall for providing access to, and dispensing of, the disposable wipe. The slot may be releasably sealed by an adhesive strip.

U.S. Patent Application 2008/0108965 to Christensen et al discloses a sanitary diaper changing kit including a package, a pair of disposable gloves in the package, and a re-sealable disposal bag in the package. Alternatively, the kit may include other materials such as small single-use package of moist wipes or towelettes, a small single-use package of antiseptic wipes, a small single use package of petroleum jelly and a small single-use package of powder. The sanitary diaper changing kit may be packaged and sold with a disposable diaper, or may be sold separately from diapers to be used in conjunction with a disposable diaper. The kit allows the person changing the diaper to be isolated from the contaminated diaper during the diaper changing operation and provides a convenient means by which the soiled diaper and other used or soiled materials may be disposed of in a sanitary procedure and diaper wearer remains isolated from care giver.

U.S. Patent Application 2008/0289993 to Flannery discloses an apparatus including a first compartment for storing and heating baby wipes, a second compartment for storing plastic bags for use as dirty diaper bags, a first fluid receptacle for holding and dispensing hand-lotion, a second fluid receptacle for holding and dispensing anti-bacterial lotion, and a tube receiving and squeezing mechanism that can hold one of a variety of tubes and that can squeeze cream such as diaper rash ointment from the tube.

U.S. Design Pat. D341,027 discloses an ornamental design for a diaper changing kit.

Although the aforementioned prior art have contributed to the development of the art of diaper changing, none of these prior art patents have solved the needs of this art.

Therefore, it is an object of the present invention to provide an improved diaper changing kit for new fathers which addresses the problems of the prior art.

Another object of this invention is to provide an improved new fathers diaper changing kit which combines humor and utility.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to a diaper changing kit for assisting an individual in cleaning a soiled child. The diaper changing kit comprises a container defining an interior chamber and a container aperture for accessing the interior chamber. A tool cleans the soiled child and provides both a functional and a humorous characteristic. A first body item is positioned on the individual and provides both a functional and a humorous characteristic. A second body item is positioned on the soiled child and provides both a functional and a humorous characteristic. The tool, the first body item and the second body item are positioned within the container for transporting.

In one embodiment of the invention, a closure is pivotably secured to the container between an open position for permitting access to the interior chamber and a closed position for covering the container aperture.

In a more specific embodiment of the invention, the tool includes tongs for griping and lifting a soiled object.

In one embodiment of the invention, the first body item includes a respirator for filtering a gas before inhalation by the individual.

In another embodiment of the invention, the second body item includes a pacifier for inserting into a mouth of the child.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
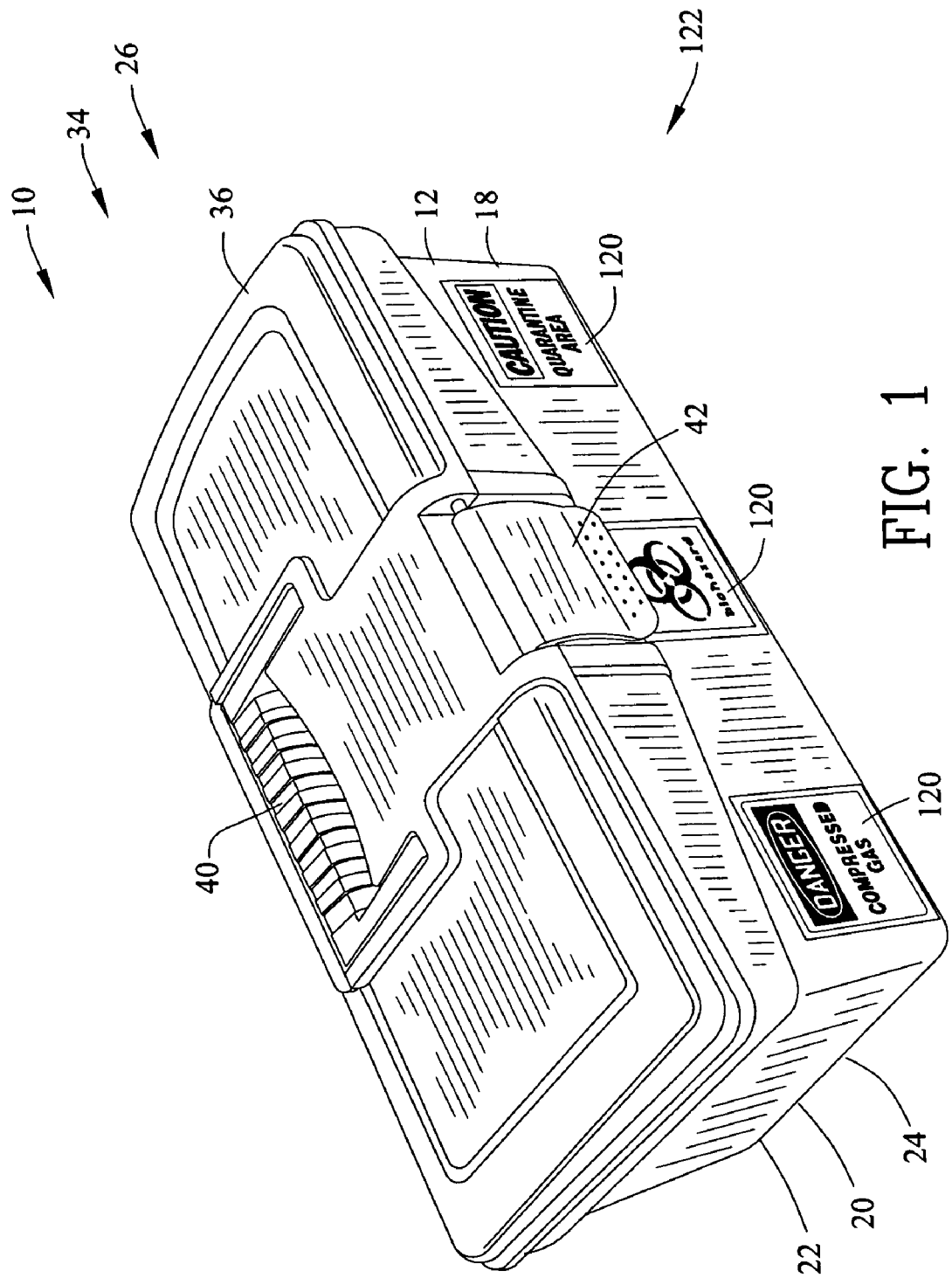
FIG. 1 is a front isometric view of a diaper changing kit of the present invention.
Figure 2:
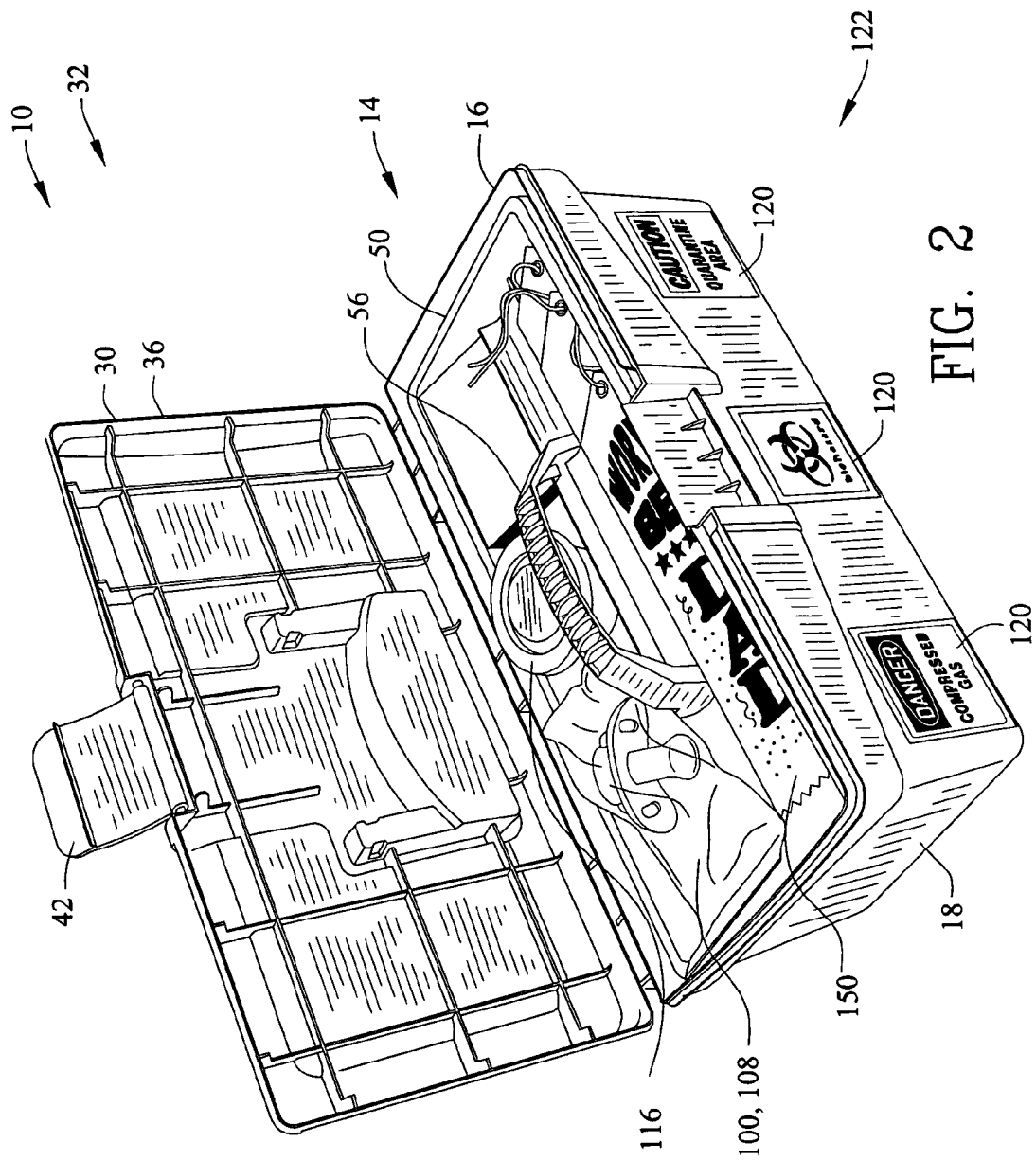
FIG. 2 is a view similar to FIG. 1 illustrating a closure in an open position.
Figure 3:
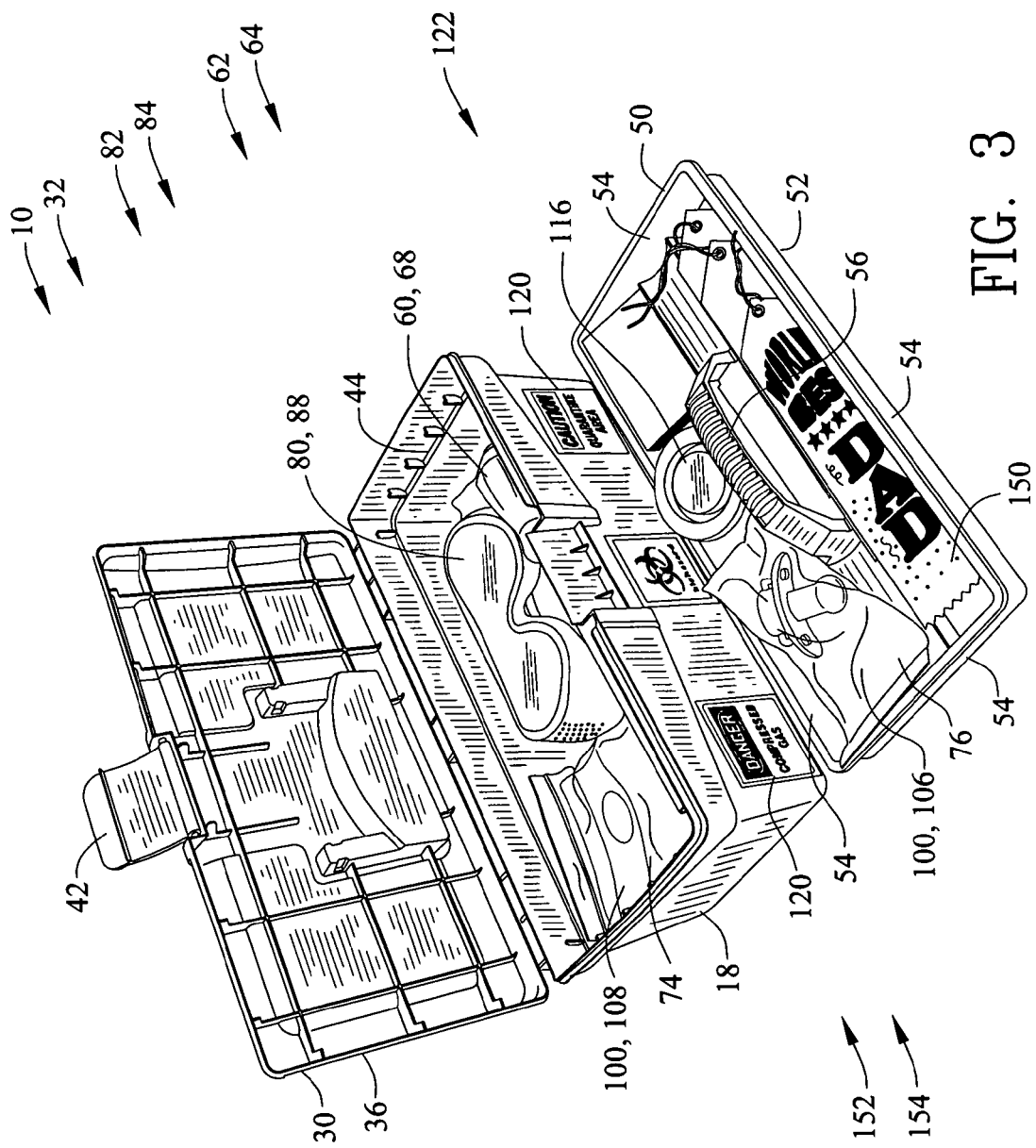
FIG. 3 is a view similar to FIG. 2 illustrating a tool tray being removed from the diaper changing kit.

FIGS. 1-4 illustrate a diaper changing kit 10 for assisting an individual in cleaning a soiled child. The diaper changing kit 10 comprises a container 12 defining an interior chamber 14 and a container aperture 16 for accessing the interior chamber 14. A closure 30 is pivotably secured to the container 12 between an open position 32 as shown in FIGS. 2 and 3. The open position 32 permits access to the interior chamber 14. The closure 30 may be positioned into a closed position 34 as shown in FIG. 1. The closed position 34 covers the container aperture 16. The interior chamber 14 may receive a tool 60, a first body item 80 and a second body item 100 that will be explained in more detail below. The tool 60, the first body item 80 and the second body item 100 may be positioned within a flexible storage container 76 for individually packaging the tool 60, the first body item 80 and the second body item 100. A label 78 may be applied to the flexible storage container 76 for indicating the contents of the flexible storage container 76 naming the tool 60, the first body item 80 and the second body item 100.

In a more specific embodiment of the invention the container 12 may include a tool box 18 constructed from a polymeric material 20. However, the container 12 may be constructed from cardboard 22 having a decorative covering 24 for providing the appearance of a tool box. Alternatively, the container 12 may include a bag or sack 26 constructed from a textile, polymeric or other flexible materials.

The closure 30 may include a tool box lid 36. Alternatively, if the container 12 includes a bag or sack 26 the closure 30 may include a bag closure such as a draw-string closure. A handle 40 is pivotably secured to the tool box lid 36 for grasping the tool box 18. A lock 42 is pivotably secured to the tool box lid 36 and engages with the tool box 18 for locking the tool box lid 36 in the closed position 34. A shoulder 44 is integral to the tool box 18 for positioning within the interior chamber 14. A tool tray 50 defines a bottom panel 52, a plurality of side walls 54 and an integral handle 56. The tool tray 59 may receive one or more of the tool 60, the first body item 80 and the second body item 100. The bottom panel 52 is positioned adjacent to the shoulder 44 for supporting the tool tray 50 within the tool box 18.

The tool 60 provides a functional characteristic 62 by utilizing the tool 60 for cleaning the soiled child. Furthermore, the tool 60 provides a humorous characteristic 64 upon delivering of the diaper changing kit 10 to the recipient, upon utilizing the tool 60 on the soiled child, general discussion of the diaper changing kit, etc. The tool 60 may include tongs 66 for griping and lifting a soiled object. The tool 60 may further include a turkey baster 68 for washing the soiled child. The tool 60 may also include child wipes 70 for cleaning the soiled child. The tool 60 may include a flexible soiled receptacle for receiving a soiled object. The flexible soiled receptacle may include a zip lock polymeric bag 74.

The first body item 80 provides a functional characteristic 82 by utilizing the first body item 80 for positioning on the individual. Furthermore, the first body item 80 provides a humorous characteristic 84 upon delivering of the diaper changing kit 10 to the recipient, upon utilizing the first body item 80 on the individual, general discussion of the diaper changing kit, etc. The first body item 80 may include a respirator 86 for filtering a gas before inhalation by the individual. The first body item 80 may further include safety goggles 88 for shielding an eye region of the individual. The first body item 80 may also include a fluid-protective apparel 90 for shielding a body portion of the individual. The fluid-protective apparel 90 may include a poncho 92. The first body item 80 may include ear plugs 94 for shielding an inter ear of the individual from sounds emitting from the soiled child. The first body item 80 may further include nose plugs 96 for shielding a nasal cavity of the individual from odors emitting from the soiled child. The first body item 80 may include rubber gloves 98 for shielding a hand portion of the individual. The first body item 80 may also include a hand wipes 99 for cleaning the individual and surrounding area.

Figure 4:
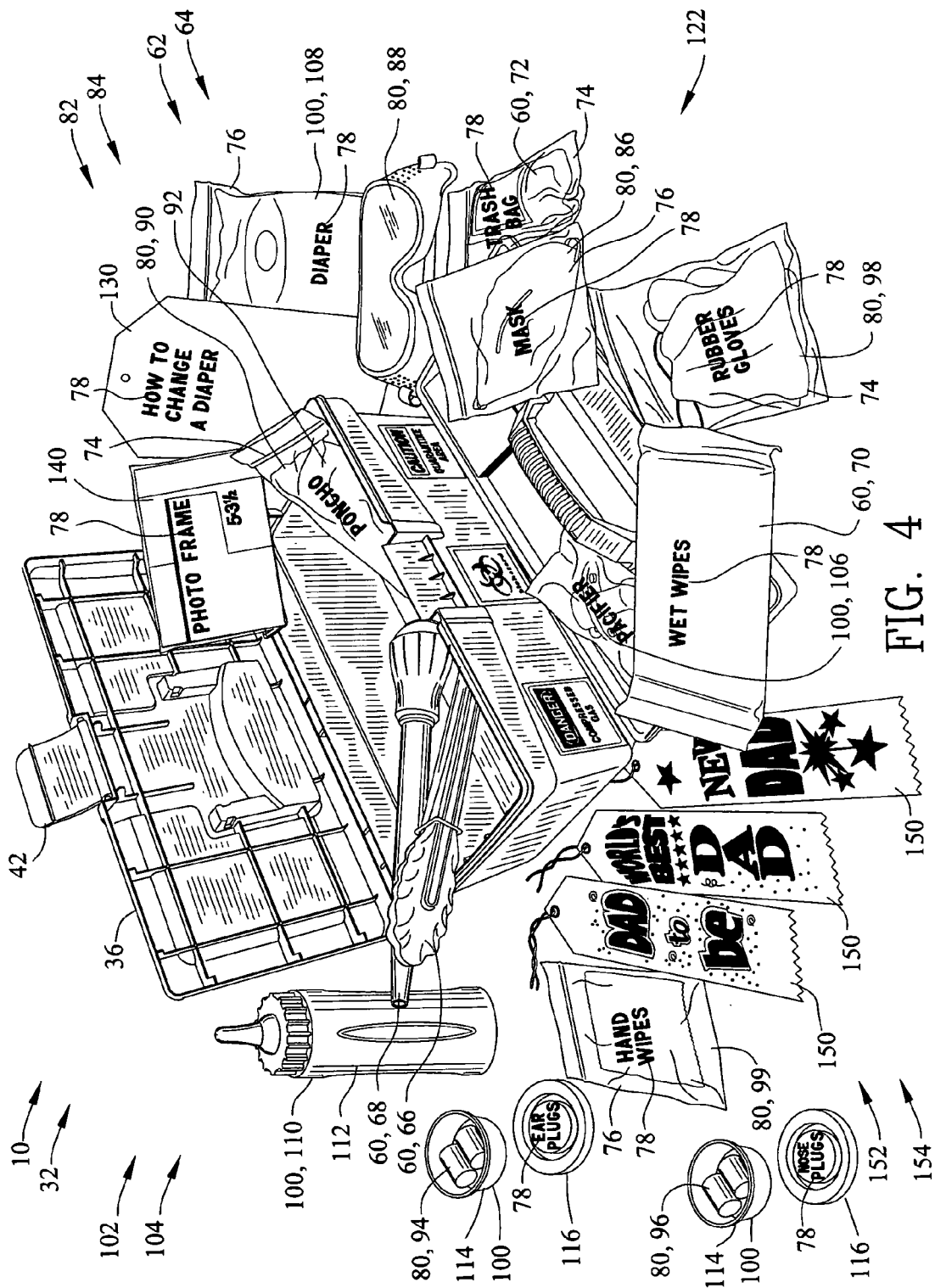
FIG. 4 is a view similar to FIG. 3 illustrating a plurality of tools and a plurality of body items surrounding the diaper changing kit.

The second body item 100 provides a functional characteristic 102 by utilizing the second body item 100 for positioning on the soiled child. Furthermore, the second body item 100 provides a humorous characteristic 104 upon delivering of the diaper changing kit 10 to the recipient, upon utilizing the second body item 100 on the soiled child, general discussion of the diaper changing kit 10, etc. The second body item 100 may include a pacifier 106 for inserting into a mouth of the child. The second body item 100 may further include diaper 108 for covering a lower torso of the child. The second body item 100 may also include a liquid container 110 for storing a liquid. The liquid container 110 may include an infant formula bottle 112. As shown in FIGS. 2-4, a soufflé cup 114 having a soufflé cup lid 116 may house the ear plugs 94 and the nose plugs 96. After removing the ear plugs 94 or the nose plugs 96 from the souffle cup 114, the soufflé cup 114 may be inverted and positioned over the groin area of the child. By utilizing the soufflé cup 114 to cover the groin area of the child prevents urinating on the individual, surrounding area and a large area of the child. As such, the souffle cup 114 may define a further second body item 100.

As shown in FIGS. 2-4, one or more tools 60, first body items 80 and/or second body times 100 may be positioned within the container 12 for transporting. In FIGS. 1-4, the container 12 includes one or more warning labels 120. The warning labels 120 provides a humorous characteristic 122 upon delivering of the diaper changing kit 10 to the recipient, upon utilizing the diaper changing kit 10 on the individual, general discussion of the diaper changing kit 10, etc.

A laminated instructional sheet 130 may also be removably positioned within the container 12. The laminated instructional sheet 130 provides a functional characteristic 132 by providing instructions for changing a child's diaper or other instructional messages. Furthermore, the laminated instructional sheet 130 provides a humorous characteristic 134 upon delivering of the diaper changing kit 10 to the recipient, upon utilizing the laminated instructional sheet 130, general discussion of the diaper changing kit, etc.

A picture frame 140 may also be removably positioned within the container 12. The picture frame 140 provides a functional characteristic 142 by receiving a photograph of an individual's first delivery of the diaper changing kit 10 or other photographs. Furthermore, the picture frame 140 provides a humorous characteristic 144 upon delivering of the diaper changing kit 10 to the recipient, upon utilizing the picture frame 140, general discussion of the diaper changing kit, etc.

An award certificate 150 may also be removably positioned within the container 12. The award certificate 150 provides a functional characteristic 152 by being secured to the individual. Furthermore, the award certificate 150 provides a humorous characteristic 154 upon delivering of the diaper changing kit 10 to the recipient, upon placement of the award certificate 150 on the individual, general discussion of the diaper changing kit, etc.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A diaper changing kit for assisting an individual in cleaning a soiled child, the diaper changing kit, comprising:
   a container defining an interior chamber and a container aperture for accessing said interior chamber;
   a tool for cleaning the soiled child providing both a functional and a humorous characteristic selected from the group consisting of a tongs and a turkey baster;
   a first body item for positioning on the individual providing both a functional and a humorous characteristic selected from the group consisting of a respirator, goggles and poncho;
   said tool and said first body item positioned within said container for transporting;
   said tongs for gripping and lifting a soiled object;
   said turkey baster for washing the soiled child;
   said respirator for filtering a gas before inhalation by the individual;
   said safety goggles for shielding an eye region of the individual; and
   said poncho for shielding a body portion of the individual.

2. A diaper changing kit as set forth in claim 1, further including a closure pivotably secured to said container between an open position for permitting access to said interior chamber and a closed position for covering said container aperture;
   said container is a tool box;
   said closure is a tool box lid;
   a handle pivotably secured to said tool box lid for grasping said tool box;
   a lock pivotably secured to said tool box lid and engaging with said tool box for locking said tool box lid in said closed position;
   a shoulder integral to said tool box for positioning within said interior chamber;
   a tool tray defining a bottom panel and a plurality of side walls for receiving one or more of said tool, said first body item and said second body item;

said bottom panel being positioned adjacent to said shoulder for supporting said tool tray within said tool box; and said container having a warning label providing humorous characteristic.

3. A diaper changing kit as set forth in claim 1, further including a laminated instructional sheet providing both a functional and a humorous characteristic; and said laminated instructional sheet positioned within said container for transporting.

4. A diaper changing kit as set forth in claim 1, further including a picture frame for housing a photograph providing both a functional and a humorous characteristic; and said picture frame positioned within said container for transporting.

5. A diaper changing kit as set forth in claim 1, further including an award certificate providing both a functional and a humorous characteristic; and said award certificate positioned within said container for transporting.

6. A diaper changing kit as set forth in claim 1, wherein said tool further includes child wipes for cleaning the soiled child.

7. A diaper changing kit as set forth in claim 1, wherein said tool further includes a flexible soiled receptacle for receiving a soiled object.

8. A diaper changing kit as set forth in claim 1, wherein said first body item further includes ear plugs for shielding an inter ear of the individual.

9. A diaper changing kit as set forth in claim 1, wherein said first body item further includes nose plugs for shielding a nasal cavity of the individual.

10. A diaper changing kit as set forth in claim 1, wherein said first body item further includes rubber gloves for shielding a hand portion of the individual.

11. A diaper changing kit as set forth in claim 1, wherein said first body item further includes hand wipes for cleaning the individual.

12. A diaper changing kit as set forth in claim 1, further including a second body item for positioning on the soiled child providing both a functional and a humorous characteristic selected from the group consisting of a diaper, a liquid container and a soufflé cup;

said second body item positioned within said container for transporting;

said diaper covering the child;

said liquid container storing a liquid; and said souffle cup covering a groin area of the child.

* * * * *